(12) United States Patent
Mattern et al.

(10) Patent No.: US 11,723,911 B2
(45) Date of Patent: *Aug. 15, 2023

(54) TREATMENT OF DEMYELINATING DISEASES

(71) Applicant: M ET P PHARMA AG, Emmetten (CH)

(72) Inventors: Claudia Mattern, Emmetten (CH); Elisabeth Traiffort, Paris (FR); Michael Schumacher, Kemlin-Bicêtre (FR)

(73) Assignee: M ET P PHARMA AG, Emmetten (CH)

( * ) Notice: Subject to any disclaimer, the term of this patent is extended or adjusted under 35 U.S.C. 154(b) by 237 days.

This patent is subject to a terminal disclaimer.

(21) Appl. No.: 17/157,337

(22) Filed: Jan. 25, 2021

(65) Prior Publication Data

US 2021/0283143 A1    Sep. 16, 2021

Related U.S. Application Data

(63) Continuation of application No. 16/815,969, filed on Mar. 11, 2020, now Pat. No. 10,898,495, which is a continuation of application No. 16/506,830, filed on Jul. 9, 2019, now Pat. No. 10,596,181, which is a continuation-in-part of application No. PCT/IB2019/050198, filed on Jan. 10, 2019.

(60) Provisional application No. 62/616,173, filed on Jan. 11, 2018.

(51) Int. Cl.
| | |
|---|---|
| *A61K 31/56* | (2006.01) |
| *A61K 31/381* | (2006.01) |
| *A61K 31/565* | (2006.01) |
| *A61K 31/4545* | (2006.01) |
| *A61K 31/568* | (2006.01) |
| *A61K 9/00* | (2006.01) |
| *A61K 31/4436* | (2006.01) |
| *A61K 31/506* | (2006.01) |

(52) U.S. Cl.
CPC .......... *A61K 31/568* (2013.01); *A61K 9/0043* (2013.01); *A61K 31/4436* (2013.01); *A61K 31/506* (2013.01)

(58) Field of Classification Search
CPC .... A61K 31/56; A61K 31/381; A61K 31/565; A61K 31/4545
USPC ................. 514/171, 177, 178, 182
See application file for complete search history.

(56) References Cited

U.S. PATENT DOCUMENTS

| | | |
|---|---|---|
| 8,574,622 B2 | 11/2013 | Mattern |
| 8,609,043 B2 | 12/2013 | Mattern |
| 8,784,869 B2 | 7/2014 | Mattern |
| 8,784,882 B2 | 7/2014 | Mattern |
| 8,877,230 B2 | 11/2014 | Mattern |
| 9,186,320 B2 | 11/2015 | Mattern |
| 9,238,072 B2 | 1/2016 | Mattern |
| 9,579,280 B2 | 2/2017 | Mattern |
| 9,801,834 B2 | 10/2017 | Mattern |
| 9,962,394 B2 | 5/2018 | Mattern |
| 10,596,181 B2 | 3/2020 | Mattern |
| 10,898,495 B2 | 1/2021 | Mattern |
| 2006/0140820 A1 | 6/2006 | Mattern |
| 2009/0227550 A1 | 9/2009 | Mattern |
| 2010/0292199 A1 | 11/2010 | Leverd et al. |
| 2011/0237562 A1 | 9/2011 | Mattern |
| 2012/0005987 A1 | 1/2012 | Mattern |
| 2015/0011610 A1 | 1/2015 | Salzer et al. |
| 2018/0200203 A1 | 7/2018 | Mattern |
| 2018/0296472 A1 | 10/2018 | Mattern |

FOREIGN PATENT DOCUMENTS

| | | |
|---|---|---|
| WO | WO-2008/040488 A1 | 4/2008 |
| WO | WO-2009/077345 A1 | 6/2009 |
| WO | WO-2012/129365 A1 | 9/2012 |
| WO | WO-2017/208209 A1 | 12/2017 |
| WO | WO-2018/134783 A1 | 7/2018 |
| WO | WO-2019/138356 A1 | 7/2019 |

OTHER PUBLICATIONS

Hadden, "Hedgehog Pathway Agonism: Therapeutic Potential Small-Molecule Development," ChemMedChem, vol. 9, pp. 27-37 (2014).
Hussain et al., "The neural androgen receptor: a therapeutic target for myelin repair in chronic demyelination," Brain, vol. 136, No. 1 (Jan. 2013).
Porcu et al., "Clobetasol and Halcinonide Act as Smoothened Agonists to Promote Myelin Gene Expression and RxR[gamma] Receptor Activation," PLOS One, vol. 10, No. 12 (Dec. 2015), pp. e0144550.
Reddy, "Neurosteroids: Endogenous Role in the Human Brain and Therapeiutc Potentials," Prog. Brain Res., vol. 186, pp. 113-137 (2010).
Rimkus et al., "Targeting the Sonic Hedgehog Signaling Pathway: Review of Smoothened and GLI Inhibitors," Cancers, vol. 8, No. 22, pp. 1-23 (2016).
Samanta et al., "Inhibition of Gli1 mobilizes endogenous neural stem cells for remyelination," Nature, vol. 526, No. 7573 (Sep. 2015), pp. 448-452.

*Primary Examiner* — Raymond J Henley, III
(74) *Attorney, Agent, or Firm* — Foley & Lardner LLP

(57) ABSTRACT

Described herein are methods of promoting remyelination in a subject suffering from demyelination diseases by administering to the subject a combination of steroid hormones and Hedgehog signaling pathway modulators. Also described are methods of administering the combination of drugs, wherein the combination of drugs are in compositions adapted for nasal administration.

20 Claims, 6 Drawing Sheets

FIG. 4A
FIG. 4B
FIG. 4C
FIG. 4D
FIG. 4E
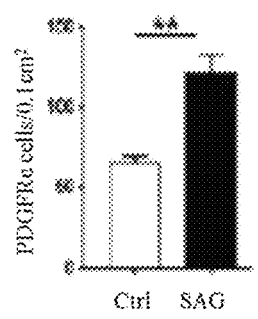
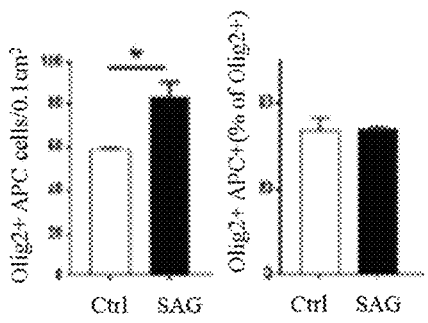
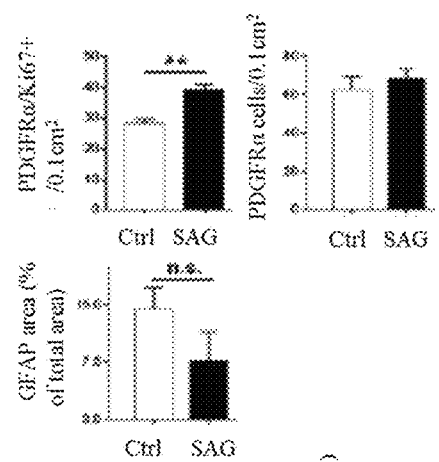
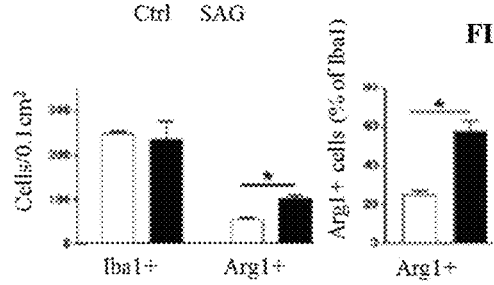

TREATMENT OF DEMYELINATING DISEASES

CROSS-REFERENCE TO RELATED APPLICATIONS

This application is a continuation of U.S. application Ser. No. 16/815,969, filed Mar. 11, 2020 (now U.S. Pat. No. 10,898,495), which is a continuation of U.S. application Ser. No. 16/506,830, filed Jul. 9, 2019 (now U.S. Pat. No. 10,596,181), which is a continuation-in-part of PCT/IB2019/050198, filed Jan. 10, 2019, which claims priority under 35 U.S.C. § 119 to U.S. provisional application 62/616,173 filed Jan. 11, 2018, the entire contents of which are incorporated herein by reference.

FIELD

Described herein are compositions and methods for treating demyelinating diseases using a steroid hormone and a Sonic hedgehog signaling pathway modulating agent.

BACKGROUND

Myelin is a fatty white substance that surrounds the axon of some nerve cells, forming an electrically insulating layer. In humans, around 40% of the brain contains white matter comprising densely packed fibers, of which myelin is a main component (50-60% dry weight of the white matter). Myelin is synthesized and maintained by oligodendrocytes (OLs) in the central nervous system (CNS). Oligodendrocytes are a type of neuroglia that function to provide support and insulation to axons in the CNS. Oligodendrocytes are generated from oligodendrocyte precursor cells (OPCs), and are found only in the CNS.

In demyelinating diseases, the myelin sheath of neurons of the nervous system is damaged. This damage may impair the conduction of signals in the affected nerves, leading to, for example, deficiency in sensation, movement, cognition, and other functions, depending on the nerves involved. Among the numerous demyelination diseases, multiple sclerosis (MS) is the most widespread disabling neurological condition of young adults around the world. The Multiple Sclerosis Foundation estimates that more than 400,000 people in the United States and about 2.5 million people around the world have MS. About 200 new cases are diagnosed each week in the United States. It is an expensive disease to treat, and the direct and indirect health care costs range from $8,528 to $54,244 per patient per year in the United States.

Multiple sclerosis disrupts the ability of parts of the nervous system to communicate, resulting in a range of physical, mental, and sometimes psychiatric problems. There is no known cure for MS, but current treatments attempt to improve function after an attack and prevent new attacks. Most medications used to treat MS may be effective in relapsing-remitting forms of the disease, but generally are ineffective in progressive forms that are characterized by a chronic demyelination of axons. Although, the immunomodulator ocrelizumab recently was shown to be effective in the progressive forms, ocrelizumab is associated with major potential side effects and poorly tolerated. See Montalban X. et al., "Ocrelizumab versus Placebo in Primary Progressive Multiple Sclerosis," *New England Journal of Medicine* 376 209-220 (2017).

In another approach, US 2013/0226133 describes a method of restoring the myelin sheath of nerve fibers using stephaglabrin sulfate. In another approach, US 2004/0141947 discloses a method for treating demyelinating CNS diseases using a colony stimulating factor or colony stimulating factor-like ligand such as sargramostim, a type 1 interferon-congener, and at least one additional therapeutic agent. In another approach, US 2004/0053850 describes a method of treating a demyelinating disease of the CNS by co-administering the tripeptide gly-pro-glu and an AMPA (α-amino-3-hydroxy-5-methyl-4-isoxazolepropionate)/kainate antagonist compound. In another approach, U.S. Pat. No. 4,760,092 claims a method of treating demyelinating diseases such as multiple sclerosis using colchicine or colchiceine. In another approach, US 2013/0302410 describes a method for neuroprotection in demyelinating diseases using dimethyl fumarate or monomethyl fumarate. In another approach, US 2013/0108643 describes a method of treating an autoimmune or inflammatory disease using an inhibitor of macrophage scavenger receptor class 1 MSR1. In another approach, EP 0423943 describes the use of an inhibitor of a member of the mammalian collagenase family of enzymes to treat demyelinating diseases.

Despite these proposed approaches, there remains a need for methods of promoting remyelination in subjects suffering from demyelinating diseases, such as MS.

SUMMARY OF THE INVENTION

In accordance with some embodiments, there are provided methods of promoting remyelination in a subject in need thereof, comprising administering to the subject an effective amount of a steroid hormone and a Hedgehog signaling pathway modulator. In some embodiments, the steroid hormone is an androgen receptor ligand such as testosterone, a progesterone receptor ligand, such as progesterone or allopregnanolone, an estrogen receptor ligands such as estradiol, or is dehydroepiandrosterone, or is a selective hormone receptor modulator such as a selective androgen receptor modulator, a selective estrogen receptor modulator, or a selective progesterone receptor modulator. In some embodiments, the Hedgehog signaling pathway modulator is a Smoothened (Smo) agonist, such as 3-Chloro-N-[trans-4-(methylamino)cyclohexyl]-N-[[3-(4-pyridinyl)phenyl]methyl]benzo[b]thiophene-2-carboxamide (SAG). In some embodiments, the Hedgehog signaling pathway modulator is a Hedgehog signaling pathway antagonist, such as a Gli antagonist. In some embodiments, the Hedgehog signaling pathway antagonist is 2,2'-[[Dihydro-2-(4-pyridinyl)-1,3(2H,4H)-pyrimidinediyl]bis(methylene)]bis[N,N-dimethylbenzenamine (GANT-61). In some embodiments, wherein the method comprising administering both a Smo agonist and a Gli antagonist, such as the Smo agonist is SAG and the Gli antagonist GANT-61.

In some embodiments, the steroid hormone and the Hedgehog signaling pathway modulator are administered in separate compositions, substantially simultaneously or sequentially. In other embodiments, the steroid hormone and the Hedgehog signaling pathway modulator are administered in the same composition.

In some embodiments, one or both of the steroid hormone and the Hedgehog signaling pathway modulator is administered intranasally in an intranasal pharmaceutical composition that further comprises: (a) at least one lipophilic or partly lipophilic carrier present in an amount of from about 60% to about 98% by weight of the formulation; (b) at least one compound having surface tension decreasing activity present in an amount of from about 1% to about 20% by weight of the formulation; and (c) at least one viscosity regulating agent present in an amount of from about 0.5% to about 10% by weight of the formulation. In some embodiments, the intranasal pharmaceutical composition comprises the steroid hormone. In some embodiments, the intranasal pharmaceutical composition comprises the Hedgehog signaling pathway modulator. In some embodiments, the intranasal pharmaceutical composition comprises the steroid hormone and the Hedgehog signaling pathway modulator. In some embodiments, the intranasal pharmaceutical composition comprises the steroid hormone, an Smo agonist, and a Gli antagonist.

In some embodiments, one or both of the steroid hormone and the Hedgehog signaling pathway modulator is administered intranasally in an intranasal pharmaceutical composition comprising a porous excipient, wherein the steroid hormone and/or the Hedgehog signaling pathway modulator is/are loaded onto a surface of the porous excipient located inside pores of the porous excipient. In some embodiments, the steroid hormone is loaded onto a surface of the porous excipient located inside pores of the porous excipient. In some embodiments, the Hedgehog signaling pathway modulator is loaded onto a surface of the porous excipient located inside pores of the porous excipient. In some embodiments, the steroid hormone and the Hedgehog signaling pathway modulator are loaded onto a surface of the porous excipient located inside pores of the porous excipient. In some embodiments, the steroid hormone, an Smo agonist, and a Gli antagonist are loaded onto a surface of the porous excipient located inside pores of the porous excipient.

In accordance with any embodiments, the subject may be a human, a non-human primate, a dog, a cat, a cow, a sheep, a horse, a rabbit, a mouse, or a rat.

In accordance with any embodiments, the subject may be suffering from a demyelinating disease, such as a demyelinating disease of the central nervous system selected from multiple sclerosis, amyotrophic lateral sclerosis, Devic's disease, inflammatory demyelinating diseases, central nervous system neuropathy, central pontine myelinolysis, myelopathies, tabes dorsalis, syphilitic myelopathy, leukoencephalopathies like progressive multifocal leukoencephalopathy, Leukodystrophies, and Alzheimer's disease, or a demyelinating disease of the peripheral nervous system selected from Guillain-Barré syndrome, chronic inflammatory demyelinating polyneuropathy, Anti-MAG peripheral neuropathy, Charcot-Marie-Tooth disease, hereditary neuropathy with liability to pressure palsy, peripheral neuropathy, myelopathy, optic neuropathy, and progressive inflammatory neuropathy.

Also provided are a steroid hormone as described herein and a Hedgehog signaling pathway modulator as described herein for use in a method as described herein for promoting remyelination in a subject in need thereof.

Also provided are uses of a steroid hormone as described herein and/or a Hedgehog signaling pathway modulator as described herein in the preparation of a medicament for treating demyelination in a subject in need thereof, wherein the method comprises administering the steroid hormone and the Hedgehog signaling pathway modulator to the subject as described herein.

In accordance with other embodiments, there are provided methods of producing oligodendroglial cells, comprising culturing primary mixed glial cells in a medium comprising a steroid hormone as described herein and a Smoothened agonist as described herein.

In accordance with other embodiments, there are provided methods of differentiating oligodendroglial cells into myelin-producing cells, comprising incubating oligodendroglial cells in a medium comprising a steroid hormone as described herein and a Hedgehog signaling pathway antagonist as described herein.

BRIEF DESCRIPTION OF THE DRAWINGS

FIG. 1A shows the relative expression of transcripts encoding myelin basic protein (Mbp). FIG. 1B shows the relative expression of the Hedgehog signaling Shh ligand. FIG. 1C shows the relative expression of the Hedgehog signaling component transcription factor Gli1. FIG. 1D shows the relative expression of the main receptor mediating androgen signaling (AR). Expression is reported relative to GAPDH, as determined by quantitative RT-PCR in the dorsal telencephalon from male (grey bars) or female (black bars) mouse pups aged 0, 3, 8 or 15 days. Sexual dimorphism is only detected for AR expression. The values reported are the mean±SEM from 3 pups per gender per age. *, $p \leq 0.05$.

FIG. 2A shows the quantification of Olig2$^+$ cells which incorporated the proliferation marker BrdU 2 hours before the end of the culture, and reveals a synergic effect of SAG (0.1 µM) and testosterone (1 µM). FIG. 2A also shows that the Smo antagonist SANT-1 (SANT-1, 0.1 µM) blocks testosterone-induced increase in Olig2$^+$ BrdU$^+$ cells. FIG. 2B shows the number of Plp$^+$GFP$^+$ oligodendroglial cells differentiated from primary mixed glial cells and thus co-express the myelin marker Mbp evaluated in the absence (Ctrl) or in the presence of SAG, SANT-1, or testosterone (T). The values reported are the mean±SEM from 3-4 independent cultures. *, $p \leq 0.05$; , $p \leq 0.01$; *, $p \leq 0.001$ compared to Ctrl. Comparisons between the different drugs are as indicated: $^\#$, $p \leq 0.05$; $^{\#\#}$, $p \leq 0.01$; $^{\#\#\#}$, $p \leq 0.001$; $^{SSS}$, $p \leq 0.001$.

FIG. 3A shows quantification of the number of oligodendroglial and astroglial cells in brain slices of the mice treated as indicated based on immunostaining of the transcription factor Olig2. FIG. 3B shows quantification of the oligodendrocyte progenitor cells (OPCs) in brain slices of the mice treated as indicated based on immunostaining of the platelet-derived growth factor receptor A (PDGFRα). FIG. 3C shows quantification of the mature oligodendrocytes (OLs) in brain slices of the mice treated as indicated based on immunostaining of the adenomatous polyposis coli (APC). FIG. 3D shows the quantification of the myelinating OLs expressing the myelin basic protein (MBP) in brain slices of the mice treated as indicated. Remarkably, the maturation into MBP$^+$ OLs which is required for axon wrapping and segment elongation induced by testosterone is potentiated by the blockade of the Hedgehog signaling. The values reported are the mean±SEM from 3-5 animals per condition. *, $p \leq 0.05$; , $p \leq 0.01$; *, $p \leq 0.001$ compared to Ctrl. Comparisons between the different drugs are as indicated: $^\#$, $p \leq 0.05$.

FIGS. 4A-4E show that the pharmacological activation of Smo enhances the density of OPCs/mature OLs and specifically promotes a precocious switch in microglia activation towards the pro-regenerative phenotype in a mouse model of demyelination of the central nervous system. FIG. 4A shows a histogram that visualizes the quantification of PDGFRα+ OPCs per unit surface based on immunostaining of brain slices derived from adult male mice 10 days after injection of lysolecithin (LPC) into the corpus callosum in the absence (Ctrl, white bars) or in the presence of SAG (black bars). FIG. 4B shows a histogram that visualizes the quantification of Olig2$^+$/APC$^+$ mature OLs per unit surface area and the percentage of Olig2+ oligodendroglial lineage cells which co-express the APC marker based on immunostaining of brain slices derived from adult male mice 10 days after injection of lysolecithin (LPC) into the corpus callosum in the absence (Ctrl, white bars) or in the presence of SAG (black bars). The values reported are the mean±SEM from n=4-6 animals per condition. FIG. 4C shows histograms quantifying Ki67+/PDGFRα+ OPCs per unit surface area based on immunostaining of brain slices derived from adult male mice 2 days after injection of lysolecithin (LPC) into the corpus callosum in the absence (Ctrl, white bars) or in the presence of SAG (black bars). FIG. 4C further shows that a higher number of proliferating OPCs are observed in the SAG-treated condition based on Ki67 and PDGFRα immunostaining (left panel), but the number of PDGFRα+ cells are unchanged by SAG treatment (right panel) at this early time point. FIG. 4D shows a histogram visualizing quantification of GFAP+ astrocytes as percentage of total area. FIG. 4E shows histograms visualizing quantification of Iba1+, Arg1+ cells per surface unit (left panel), and Arg1+ cells as percentage of Iba1+ cells (right panel) based on immunostaining of brain slices derived from adult male mice 2 days after injection of lysolecithin (LPC) into the corpus callosum in the absence (Ctrl, white bars) or in the presence of SAG (black bars). FIG. 4E further shows that a much higher number of Arg-1$^+$ pro-regenerative microglia is detected in the lesion of SAG-treated animals.

FIG. 5A shows EAE clinical scores after therapeutic administration of SAG and testosterone used separately or simultaneously compared with vehicle administration. FIG. 5B shows electron micrographs from the lumbar spinal cord of vehicle (Ctrl), testosterone (T), SAG and SAG+T-treated EAE mice. Besides normal myelinated axons (right-most arrow), demyelinated (bottom-most arrow) and abnormal (left-most arrow) axons are observed at a higher level in the control condition. FIG. 5C shows an analysis of the g-ratio (axon diameter/axon+myelin diameter) and indicates that the values are significantly lower when testosterone and SAG are used separately or simultaneously as compared to the control. SAG alone or with testosterone displays a significantly higher effect on the g-ratio than testosterone alone. FIG. 5D shows the quantification of abnormal axons, including axons exhibiting myelin still compacted but detached from the axon, double myelin sheaths or multilayered myelin where the inside of the axon was obstructed. The percentage of abnormalities among the total number of axons is significantly decreased under treatment conditions compared to the control. FIG. 5F-5F show the quantification of the area occupied by Iba1$^+$ (FIG. 5E) and Arg1$^+$ (FIG. 5F) cells expressed as a percentage of the total area of the lesion in the image based on immunostaining of Iba and Arg1 of the lumbar spinal cord of EAE animals treated by the vehicle (Ctrl) or by the drugs testosterone and SAG used separately or simultaneously.

DETAILED DESCRIPTION

Figure 1A:
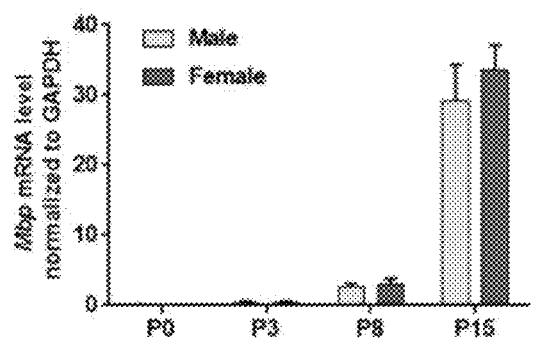
FIGS. 1A-1D show that Hedgehog and androgen hormone signaling components are dynamically transcribed during the last wave of oligodendrogenesis and the myelination process in the early postnatal dorsal telencephalon.

Described herein are methods of promoting remyelination in a subject in need thereof that comprise administering to the subject an effective amount of a steroid hormone and a Hedgehog signaling pathway modulator. In some embodiments, the methods are for treating a demyelinating disease, such as MS. Also described are related compositions and uses of a steroid hormone and a Hedgehog signaling pathway modulator. Further described are compositions and methods using a steroid hormone, a Smoothened agonist, and a Hedgehog signaling pathway antagonist. Also described are in vitro methods of producing proliferating oligodendroglial cells that involve culturing primary mixed glial cells in a medium comprising a steroid hormone and a Smo agonist. Also described are in vitro methods of differentiating oligodendroglial cells into myelin-producing cells that involve incubating oligodendroglial cells in a medium comprising a steroid hormone and an Smo antagonist.

Definitions

Technical and scientific terms used herein have the meanings commonly understood by one of ordinary skill in the art to which the present invention pertains, unless otherwise defined. Materials, reagents and the like to which reference is made in the following description and examples are obtainable from commercial sources, unless otherwise noted.

As used herein, the singular forms "a," "an," and "the" designate both the singular and the plural, unless expressly stated to designate the singular only.

The term "about" means that the number comprehended is not limited to the exact number set forth herein, and is intended to refer to numbers substantially around the recited number while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

As used herein, "Smoothened" or "Smo" is a 7-transmembrane GPCR-like receptor that is primarily located in the membrane of intracellular vesicles or at the plasma membrane when it is activated. Smo is a component of the Sonic Hedgehog (Shh) signaling pathway. The Shh pathway acts to control oligodendrocyte generation during embryonic development. See e.g. Traiffort E. et al., "Hedgehog: A key signaling in the development of the oligodendrocyte lineage," *Dev. Biol.* 4:28 (2016); Ferent and Traiffort, "Hedgehog: Multiple Paths for Multiple Roles in Shaping the Brain and Spinal Cord," *Neuroscientist* 21:356-71 (2015).

As used herein, "subject" denotes any mammal in need of treatment for a demyelinating disease or condition or in need of promotion of remyelination, including humans. For example, a subject may be suffering from or at risk of developing a demyelinating disease or condition.

As used herein, the term "administering" includes directly administering to another, self-administering, and prescribing or directing the administration of an agent as disclosed herein.

As used herein, the phrases "effective amount" and "therapeutically effective amount" mean that active agent dosage or plasma concentration in a subject, respectively, that provides the specific pharmacological effect for which the active agent is administered in a subject in need of such treatment. It is emphasized that an effective amount of an active agent will not always be effective in treating the conditions/diseases described herein, even though such dosage is deemed to be an effective amount by those of skill in the art.

As used herein, the term "pharmaceutical composition" refers to one or more active agents formulated with a pharmaceutically acceptable carrier, excipient or diluent.

The phrase "pharmaceutically acceptable" is employed herein to refer to those compounds, materials, compositions, and/or dosage forms which are, within the scope of sound medical judgment, suitable for use in vivo without excessive toxicity, irritation, allergic response, or other problem or complication, commensurate with a reasonable benefit/risk ratio.

Methods of Promoting Remyelination

The methods described herein are based on the surprising discovery that treatment with a steroid hormone and Hedgehog signaling pathway modulator dramatically increases the number of oligodendrocytes and myelin-producing cells. Although therapies using only a steroid hormone or only an Hedgehog signaling pathway modulator have been described (see, e.g., El-Etr et al., "Hormonal influences in multiple sclerosis: new therapeutic benefits for steroids," *Maturitas* 68:47-51 (2011); Bielecki et al., "Unexpected central role of the androgen receptor in the spontaneous regeneration of myelin," *Proc. Natl. Acad. Sci.* 113:14829-14834 (2016); Samanta et al., "Inhibition of Gli1 mobilizes endogenous neural stem cells for remyelination," *Nature* 15:448-52 (2015); US 2015/0011610; Ferent et al., "Sonic Hedgehog signaling is a positive oligodendrocyte regulator during demyelination," *J. Neuroscience* 33:1759-72 (2013)), the present inventors found that using a steroid hormone together with a Hedgehog signaling pathway modulator synergistically enhances production of oligodendrocytes and myelin producing cells, leading to improved promotion of remyelination and offering more effective treatments for demyelinating diseases.

In this regard, the present inventors discovered an overlapping expression pattern of Shh signaling components and the androgen receptor during early development of oligodendrocytes. See Example 1, FIG. 1. These expression patterns appeared to be consistent with the first demonstration of a functional interaction between Shh signaling and steroid hormones during the myelination process. Indeed, the inventors discovered that treatment with an androgen (such as testosterone) can promote the proliferation of oligodendrocyte precursor cells at a higher level in the presence of an Smo agonist as compared to in the absence of an Smo agonist. In addition, it was found that the concomitant use of an Smo antagonist and testosterone promotes the differentiation of myelin producing cells in a synergistic manner. See Example 1, FIG. 2, and Example 1, FIG. 3. These results support the methods described herein.

The present inventors also surprisingly discovered that, in the context of myelin repair, a Smo agonist promotes a precocious switch in microglia activation towards the pro-regenerative phenotype and can act synergistically with a steroid hormone (such as testosterone) to promote remyelination, as shown in the examples reported below. These results also support the methods described herein.

Steroid Hormones

Steroid hormones useful in the compositions and methods described herein include but are not limited to steroid hormones of the progestogen, estrogen, and androgen families, synthetic steroid hormones, and selective hormone receptor modulators.

In some embodiments, the steroid hormone is an androgen receptor ligand (e.g., an androgen). Androgens are a group of steroid hormones that mediate their effects through binding and activation of the androgen receptor (AR). As used herein, androgens include testosterone and dihydrotestosterone. In specific embodiments, the steroid hormone is the androgen testosterone.

In some embodiments, the steroid hormone is a progestogen. Progestogens are a group of steroid hormones that mediate their effects through binding and activation of the progesterone receptor (PR). In some specific embodiments, the progestogen is progesterone or allopregnanolone, which is derived from progesterone and activates the γ-aminobutyric acid (GABA) receptor.

In some embodiments, the steroid hormone is an estrogen receptor ligand (e.g., an estrogen). Estrogens are a group of steroid hormones that mediate their effects through binding and activation of the estrogen receptor (ER). As used herein, estrogens include estradiol.

In some embodiments, the steroid hormone is dehydroepiandrosterone (DHEA). DHEA can serve as precursor for both androgenic and estrogenic steroids.

In some embodiments, the steroid hormone is a synthetic steroid.

In some embodiments, a selective hormone receptor modulator is used as a "steroid hormone" in the methods described herein. Selective hormone receptor modulators function similarly to steroid hormone but generally are more selective than steroids per se. As used herein, "selective hormone receptor modulators" include, but are not limited to, selective androgen receptor modulators, selective estrogen receptor modulators, and selective progesterone receptor modulators.

Hedgehog Signaling Pathway Modulators

Hedgehog signaling pathway modulators useful in the compositions and methods described herein include Smo agonists that increase Shh signaling and Smo antagonists that decrease Shh signaling, as well as Gli antagonists.

Thus, in some embodiments, the Hedgehog signaling pathway modulator is an Smoothened (Smo) agonist. Smo agonists may interact with Smo receptors to activate the downstream Gli transcription factor. See, e.g., Hadden et al., "Hedgehog Pathway Agonism: Therapeutic Potential and Small-Molecule Development." *Chem. Med. Chem.* 9:27-37 (2014); Chen et al., "Small molecule modulation of Smoothened activity," *Proc. Natl. Acad. Sci.* 99:14071-14076 (2002). Examples of Smoothened agonists include 3-Chloro-N-[trans-4-(methylamino)cyclohexyl]-N-[[3-(4-pyridinyl)phenyl]methyl]benzo[b]thiophene-2-carboxamide (SAG), 3-chloro-4,7-difluoro-N-(4-(methylamino)cyclohexyl)-N-(3-(pyridin-4-yl)benzyl)benzo[b]thiophene-2-carboxamide (Hh Ag-1.5), glucocorticoids, 9H-Purin-6-amine, 9-cyclohexyl-N-[4-(4-morpholinyl)phenyl]-2-(1-naphthalenyloxy) (Purmorphamine), propyl 4-(1-hexyl-4-hydroxy-2-oxo-1,2-dihydroquinoline-3-carboxamido) benzoate (GSA-10), cholesterol, and osteogenic (1H)-quinolone-based compounds such as GSA-10 like compounds 20 and 25 (Manetti et al., "Design, synthesis and biological characterization of a new class of osteogenic (1H)-quinolone derivatives," *Eur. J. Med. Chem.* 121:747-757 (2016)). In specific embodiments, the Hedgehog signaling pathway modulator is the Smo agonist 3-Chloro-N-[trans-4-(methylamino)cyclohexyl]-N-[[3-(4-pyridinyl)phenyl]methyl]benzo[b]thiophene-2-carboxamide (SAG).

In some embodiments, the Hedgehog signaling pathway modulator is a Gli antagonist. Gli antagonists include but are not limited to, small molecule Gli1 antagonists such as 2,2'-[[Dihydro-2-(4-pyridinyl)-1,3(2H,4H)-pyrimidinediyl]bis(methylene)]bis[N,N-dimethyl-benzenamine (GANT61) and 2,3,4,5-Tetra(4-pyridyl)thiophene, 4,4',4'',4'''-Thiene-2,3,4,5-tetrayltetrapyridine (GANT58) disclosed in Lauth et al., "Inhibition of GLI-mediated transcription and tumor cell growth by small-molecule antagonists," *Proc. Natl. Acad. Sci.* 104: 8455-60 (2007). Both GANT61 and GANT58 are believed to act in the nucleus to block Gli function, and GANT61 is believed to interfere with DNA binding of Gli1. In specific embodiments, the Hedgehog modulator is the Gli antagonist GANT61.

Other Hedgehog signaling pathway modulators are Smo antagonists, such as disclosed in Chen (2002) (supra) and Rimkus et al., "Targeting the Sonic Hedgehog signaling pathway: Review of Smoothened and Gli inhibitors," *Cancers* 8: pii:E22 (2016), including (4-Benzyl-piperazin-1-yl)-(3,5-dimethyl-1-phenyl-1H-pyrazol-4-ylmethylene)-amine (SANT-1), N-[3-(1H-Benzimidazol-2-yl)-4-chlorophenyl]-3,4,5-triethoxybenzamide SANT-2, and (4-Benzyl-piperazin-1-yl)-(3,5-dimethyl-1-phenyl-1H-pyrazol-4-ylmethylene)-amine (SANT-3), and SANT-4, which has the following structure:

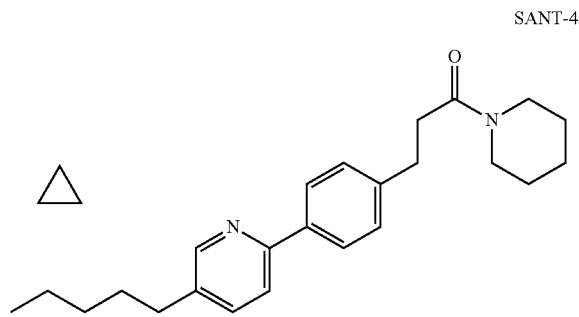

SANT-4

In some embodiments, both an Smo agonist and a Gli antagonist are used as Hedgehog signaling pathway modulators. That is, in some embodiments, the Hedgehog signaling pathway modulator includes both an Smo agonist and a Gli antagonist. As such, in some embodiments, a steroid hormone, an Smo agonist and a Gli antagonist are used or administered as described herein.

Pharmaceutical Compositions

The steroid hormone and Hedgehog signaling pathway modulator can be administered in separate compositions (substantially simultaneously or sequentially), or they can be administered in the same composition.

The composition(s) can be any pharmaceutical compositions suitable for administering the steroid hormone and/or Hedgehog signaling pathway modulator, formulated for any route of administration. Suitable routes of administration may, for example, include oral, rectal, transmucosal, especially intranasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections. Some embodiments involve oral administration. Some embodiments involve intranasal administration.

In some embodiments, the steroid hormone and/or Hedgehog signaling pathway modulator is formulated in an intranasal pharmaceutical composition. As used herein "intranasal composition" means a composition suitable for, or adapted for, intranasal delivery. Such embodiments may offer enhanced uptake of the steroid hormone and/or Hedgehog signaling pathway modulator.

Exemplary oleogel-type intranasal pharmaceutical compositions for testosterone have been described, for example, in U.S. Pat. No. 8,574,622, the entire contents of which are incorporated herein by reference. In some embodiments, one or both of the steroid hormone and the Hedgehog signaling pathway is formulated in an intranasal pharmaceutical composition as described in U.S. Pat. No. 8,574,622, such as a composition that includes the active agent(s) and that further comprises: (a) at least one lipophilic or partly lipophilic carrier present in an amount of from about 60% to about 98% by weight of the formulation; (b) at least one compound having surface tension decreasing activity present in an amount of from about 1% to about 20% by weight of the formulation; and (c) at least one viscosity regulating agent present in an amount of from about 0.5% to about 10% by weight of the formulation.

In such oleogel embodiments, the lipophilic or partly lipophilic carrier may be any such carrier suitable as a carrier or vehicle for a nasal pharmaceutical composition, such as an oil, such as a vegetable oil, such as castor oil, hydrogenated castor oil, soybean oil, sesame oil, or peanut oil, or any vehicle discussed below that is lipophilic or partly lipophilic, or any other suitable lipophilic or partly lipophilic carrier.

In such oleogel embodiments, the compound(s) having surface tension decreasing activity may be one or more surfactants such as lecithin, fatty acid esters of polyvalent alcohols, of sorbitanes, of polyoxyethylensorbitans, of polyoxyethylene, of sucrose, of polyglycerol and/or one or more humectants such as sorbitol, glycerine, polyethylene glycol, and macrogol glycerol fatty acid esters, or one or more oleoyl macrogolglycerides (such as LABRAFIL® M 1944 CS, available from Gattefosse (France), or any surfactant discussed below, or any other suitable surfactant.

In such oleogel embodiments, the viscosity regulating agent(s) may be one or more selected from thickeners and gelling agents, such as cellulose and cellulose derivatives, polysaccharides, carbomers, polyvinyl alcohols, povidone, colloidal silicon dioxide, cetyl alcohols, stearic acid, beeswax, petrolatum, triglycerides and lanolin, or any viscosity regulating agent discussed below, or any other suitable surfactant.

Other exemplary intranasal pharmaceutical compositions include those described in U.S. patent application Ser. No. 15/612,454, the entire contents of which are incorporated herein by reference. U.S. patent application Ser. No. 15/612,454 describes intranasal pharmaceutical compositions wherein an active agent is loaded onto a porous agent. Thus, in some embodiments, one or both of the steroid hormone and the Hedgehog signaling pathway modulator is formulated in an intranasal pharmaceutical composition as described in U.S. patent application Ser. No. 15/612,454, such as a composition comprising a porous agent, wherein the steroid hormone and/or the Hedgehog signaling pathway modulator is/are loaded onto a surface of the porous agent located inside pores of the porous agent. As described in U.S. Ser. No. 15/612,454, the active-agent loaded porous agent may itself be formulated in an oleogel composition, such as described those in U.S. Pat. No. 8,574,622.

In such porous agent embodiments, the porous agent may comprise an inorganic porous material, such as colloidal silicon dioxide, micro-porous silicon dioxide, meso-porous silicon dioxide, macro-porous silicon dioxide, polyorganosiloxanes, pharmaceutical clays, silicon dioxide nanotubes, silicon dioxide gel, magnesium alumosilicate (such as but not limited to VEEGUM® from Vanderbilt Minerals, LLC), activated carbon, anhydrous calcium phosphate, calcium carbonate, alumina, and combinations of any two or more thereof. Exemplary inorganic porous materials include porous silicon dioxide commercially available under the SYLOID® brand from W.R. Grace & Co. (such as but not limited to SYLOID® 244FP, 72FP, XDP6035 (also known as SILSOL™ 6035), XDP3050, XDP3150, AL-1FP, and combinations of any two or more thereof), porous silicon dioxide available under the AEROPERL® brand from Evonik Industries, Corp. (such as but not limited to AEROPERL® 300, which has a surface area of about 260 to 320 $m^2/g$ (such as about 300 $m^2/g$), a pore volume of about 1.5 to 1.9 ml/g, and an average particle size of about 20 to about 60 μm), silicon dioxide PARTECK® SLC from EMD Millipore, NEUSILIN® (a synthetic, amorphous form of magnesium aluminometasilicate) from Fuji Chemical Industry, Zeolite Socony Mobil-5, Mobil Composition of Matter No. 41, SBA-15, FDU-11, OMS-7, OMS-Lemon-7, and IITM-56. In some embodiments, the porous agent comprises silicon-based powders, which may be hydrophobic or hydrophilic, e.g., depending on groups chemically bonded to their surfaces.

In some embodiments, the porous agent comprises an organic-inorganic hybrid, such as metal-organic frameworks (MOFs). Exemplary hybrid materials can be formed by self-assembly of polydentate bridging ligands and metal connecting points.

In some embodiments, the porous agent comprises organic polymers, such as microporous organic polymers, polystyrene, cellulose, and/or poly(methyl methacrylate). In some embodiments, microporous organic polymers are formed by carbon-carbon coupling reactions and comprised of non-metallic elements such as carbon, hydrogen, oxygen, nitrogen, and/or boron. In some embodiments, organic polymers are produced by emulsion polymerization and hypercrosslinking followed by chemical etching of sacrificial $SiO_2$ cores. In some embodiments, networks of organic polymers are constructed from small organic building blocks.

In some embodiments, the porous agent comprises porous materials based on complexing agents, such as an ion exchange resin (such as but not limited to cross-linked polystyrene) or an adsorbent (such as but not limited to β-cyclodextrin-based porous silica, α-cyclodextrin-based porous silica, hydroxypropyl-β-cyclodextrin-based porous silica, and porous materials based on other adsorbent resins).

In some embodiments, the surface of the porous agent—including the inner pore surface—is functionalized to bind the active agent(s) and/or control release of the active agent(s) after a certain amount of time or in response to a stimulus.

The active agent-loaded porous agent may be formulated in any vehicle suitable as a vehicle for a nasal pharmaceutical composition. In some embodiments, the vehicle for the porous agent is a hydrophilic vehicle. In some embodiments, the vehicle is a lipophilic or partly lipophilic vehicle, such as a vehicle comprising one or more fats, oils, waxes, phospholipids, steroids (e.g., cholesterol), sphingolipids, ceramides, sphingosines, prostaglandins, and/or fat-oil vitamins. In some embodiments, the vehicle comprises an oil or a mixture of oils, such as vegetable oil, castor oil, hydrogenated castor oil, soybean oil, sesame oil, or peanut oil; fatty acid esters, such as ethyl- and oleyl-oleate, isopropylmyristate; medium chain triglycerides; glycerol esters of fatty acids; polyethylene glycol; phospholipids; white soft paraffin; or combinations of any two or more thereof.

The vehicle may be present in any suitable amount, such as an amount effective to provide desired properties for nasal administration, desired physical properties, desired release properties, desired pharmacokinetics, etc. In some embodiments, the composition comprises a vehicle in an amount of from about 15% to about 98% by weight, about 30 to about 98% by weight, about 50% to about 95% by weight, about 75% to about 95% by weight, about 80%, or about 90% by weight, based on the total weight of the composition. In some embodiments, the composition comprises a vehicle in an amount of from 15% to 98% by weight, 30 to 98% by weight, 50% to 95% by weight, 75% to 95% by weight, 80%, or 90% by weight, based on the total weight of the composition.

The active agent-loaded porous agent may be formulated with one or more compounds having surface decreasing activity, e.g., surfactants. The surfactant, if present, may be any surfactant suitable for use as a surfactant in a nasal pharmaceutical composition. In some embodiments, the surfactant is selected from anionic, cationic, amphoteric, and non-ionic surfactants, including, but not limited to, lecithin, fatty acid esters of polyvalent alcohols, fatty acid esters of sorbitanes, fatty acid esters of polyoxyethylensorbitans, fatty acid esters of polyoxyethylene, fatty acid esters of sucrose, fatty acid esters of polyglycerol, oleoyl polyoxylglycerides (such as but not limited to apricot kernel oil PEG-6-esters), oleoyl macrogolglycerides, and/or humectants such as sorbitol, glycerine, polyethylene glycol, macrogol glycerol fatty acid ester, and combinations of any two or more thereof. In some embodiments, the surfactant comprises an oleoyl macrogolglyceride (such as LABRAFIL® M 1944 CS (Gattefosse, Saint-Priest, France)) or a mixture of oleoyl macrogolglycerides.

The active agent-loaded porous agent may be formulated with one or more viscosity-regulating agents, which may be any viscosity-regulating agent suitable for use as a viscosity-regulating agent in a nasal pharmaceutical composition. In some embodiments, the viscosity-regulating agent comprises mesoporous silica (which may be loaded with active agent or unloaded). In some embodiments, the viscosity-regulating agent comprises cellulose, cellulose-containing substances, polysaccharides, carbomers, polyvinyl alcohol, povidone, colloidal silicon dioxide, cetyl alcohols, stearic acid, beeswax, petrolatum, triglycerides, lanolin, or combinations of any two or more thereof. In some embodiments, the viscosity-regulating agent comprises colloidal silicon dioxide (such as but not limited to AEROSIL® 200 (Evonik) and/or CAB-O-SIL® M5 (Cabot)). In some embodiments, the viscosity-regulating agent comprises synthetic silica, such as SYLODENT® (precipitated silica with a compacted bulk density of about 110 kg/m$^3$, a specific surface area of about 190 m$^2$/g, and an average particle size of about 18 μm) or SYLOBLANC® silicas (porous silica gel with a pore volume of about 1.6 ml/g and an average particle size of about 3 μm) from W.R. Grace & Co. In some embodiments, the viscosity-regulating agent comprises hydrophilic fumed silica, such as AEROSIL® 200 and/or lipophilic silicon dioxide, such as AEROSIL® R972 (which is fumed silica after-treated with dimethyldichlorosilane, and which has a surface area of about 90 to about 130 m$^2$/g). Without being bound by theory, it is believed that hydrophilic fumed silica can be used to prepare a thixotropic gel composition with a high temperature stability as compared to a comparable gel produced with other viscosity-regulating agents.

The viscosity-regulating agent, if present, may be present in an amount effective to adjust the viscosity of the composition to the desired level. In some embodiments, the composition comprises from about 0.5 to about 20% by weight, about 0.5 to about 10% by weight, about 0.5 to about 7% by weight, about 1 to about 4% by weight, about 4% by weight, or about 2% by weight viscosity-regulating agent, based on the total weight of the composition. In some embodiments, the composition comprises from 0.5 to 20% by weight, 0.5 to 10% by weight, 0.5 to 7% by weight, 1 to 4% by weight, 4% by weight, or 2% by weight viscosity-regulating agent, based on the total weight of the composition.

Regardless of the specific formulation used, the steroid hormone and Hedgehog signaling pathway modulator are formulated to provide a therapeutically effective amount of the active agents in doses suitable for the route of administration, such as a volume of composition suitable for administration to one or both nostrils, a volume suitable for oral administration, or a volume suitable for intravenous, subcutaneous, or intramuscular administration.

Methods of Use

As noted above, in accordance with the methods and uses described herein, the steroid hormone and Hedgehog signaling pathway modulator are administered to a subject in need thereof, such as a subject in need of promotion of remyelination and/or a subject in need of treatment for a demyelinating disease or condition. The subject may be any mammal, such as a human, non-human primate, dog, cat, cow, sheep, horse, rabbit, mouse, or rat.

Demyelinating diseases can be divided in those affecting the central nervous system and those affecting in the peripheral nervous system, which present different demyelination conditions. In some embodiments, the subject is suffering from a demyelination disease of the CNS such as multiple sclerosis, amyotrophic lateral sclerosis, Devic's disease, inflammatory demyelinating diseases, central nervous system neuropathy, central pontine myelinolysis, myelopathies, tabes dorsalis, syphilitic myelopathy, leukoencephalopathies (including progressive multifocal leukoencephalopathy), leukodystrophies, and Alzheimer's disease. In some embodiments, the subject is suffering from a demyelination disease of the peripheral nervous system such as Guillain-Barré syndrome, chronic inflammatory demyelinating polyneuropathy, anti-Myelin Associated Glycoprotein peripheral neuropathy, Charcot-Marie-Tooth disease, hereditary neuropathy with liability to pressure palsy, peripheral neuropathy, myelopathy, optic neuropathy, and progressive inflammatory neuropathy.

As noted above, the steroid hormone and Hedgehog signaling pathway modulator can be administered in separate compositions (substantially simultaneously or sequentially in any order), or can be administered in the same composition. As also noted above, in any embodiments, the steroid hormone and Hedgehog signaling pathway modulator can be administered by any suitable route of administration, including intranasal, oral, intravenous, subcutaneous and intramuscular. When the steroid hormone and Hedgehog signaling pathway modulator are administered in different compositions, they can be administered by the same or different routes of administration, such as oral or intranasal. In specific embodiments, the steroid hormone is administered orally or intranasally. Independently, in specific embodiments, the Hedgehog signaling pathway modulator is administered orally or intranasally.

As also noted above, the steroid hormone and Hedgehog signaling pathway modulators are administered in amounts effective to promote remyelination. As used herein, the term "remyelination" refers to the generation of new myelin sheaths. Remyelination can be assessed by methods such as direct determination of the state of myelin in the subject, such as by measuring white matter mass using magnetic resonance imaging (MRI), measuring the thickness of myelin fibers using a magnetic resonance spectroscopy (MRS) brain scan, or any other direct measures (e.g., Positron-Emission Tomography (PET), Diffusion-Weighted Imaging (DW-I, or DW-MRI), Diffusion Tensor Imaging, Myelography, Magnetization Transfer, etc.). Additionally or alternatively, remyelination can be assessed by detecting a reduction in the size or number of inflammatory lesions (i.e., scleroses) present in the patient, monitoring a patient's cerebrospinal fluid (which may be obtain, e.g., by lumbar puncture) for a reduction in the presence or amount of, e.g., (i) abnormal proteins such as tiny fragments of myelin, (ii) elevated levels of or specific types of lymphocytes, and/or (iii) abnormal levels of immunoglobulin (IgG) molecules; monitoring a patient for a positive change in neuropsychology (e.g., the status of various abilities such as memory, arithmetic, attention, judgment and reasoning); and/or monitoring a patient's urine for a decrease in levels of myelin basic protein-like material (MBPLM). Any one or more of these methodologies can be used to assess remyelination, or an alternative method can be used. The methods described herein are not limited by these or other specific methodologies for assessing remyelination.

In some embodiments, the steroid hormone is testosterone and is administered at a dose of from about 0.05 to about 0.5 mg/day, including from about 0.1 to about 0.3 mg/day, including about 0.2 mg/day. In embodiments using a different androgen receptor ligand, a corresponding molar amount of the androgen receptor ligand can be used.

In some embodiments, the Hedgehog signaling pathway modulator is SAG, and is administered at a dose of from about 5 to about 25 mg/kg body weight of the subject, including from about 10 to about 20 mg/kg, including 15 mg/kg. In embodiments using a different Smo agonist, a corresponding molar amount of Smo agonist can be used.

In some embodiments, the Hedgehog signaling pathway modulator is GANT-61, and is administered at a dose of from about 5 to about 25 mg/kg body weight of the subject, including from about 10 to about 20 mg/kg, including about 15 mg/kg. In embodiments using a different Hedgehog signaling pathway antagonist, a corresponding molar amount of Hedgehog signaling pathway antagonist can be used.

In some embodiments, the amounts of one or both of the steroid hormone and Hedgehog signaling pathway modulators administered is effective to potentiate the remyelination-promoting activity of the other. Thus, in some embodiments, the amount of steroid hormone administered with a given amount of Hedgehog signaling pathway modulator is more effective in promoting remyelination than the same amount of Hedgehog signaling pathway modulator alone. Additionally or alternatively, in some embodiments, the amount of Hedgehog signaling pathway modulator administered with a given amount of steroid hormone is more effective in promoting remyelination than the same amount of steroid hormone alone.

Also provided are steroid hormone and an Hedgehog signaling pathway modulator as described herein, for use in a method of promoting remyelination in a subject in need thereof, or for treating a demyelinating disease or condition, as discussed above.

Also provided are uses of a steroid hormone and an Hedgehog signaling pathway modulator as described herein, in the preparation of a medicament as described herein, for use in a method of promoting remyelination in a subject in need thereof, or for treating a demyelinating disease or condition, as discussed above.

As noted above and shown in the examples, the present inventors found that the use of a steroid hormone (such as testosterone) and a Smo agonist (such as SAG) synergistically promotes the production of oligodendrocytes and mitigates the course of autoimmune encephalomyelitis in experimental models. Furthermore, the use of a steroid hormone (such as testosterone) and a Gli antagonist (such as GANT61) may synergistically promote the production of myelin producing cells.

The following examples are provided to illustrate the invention, but it should be understood that the invention is not limited to the specific conditions or details of these examples.

EXAMPLES

Materials and Methods

Handling of animals. Wild-type gonadally intact or castrated C57Bl/6 male mice were purchased at the age of 8 to 12 weeks from Janvier Labs Breeding Center (France). For in vitro experiments, litters were obtained from timely mated C57Bl/6 females purchased from Janvier Labs Breeding Center or were in-house bred and mated with Plp-EGFP mice obtained from Dr. Wendy Macklin (University of Colorado, USA). See Mallon et al., *J. Neuroscience* 22: 876-885 (2002). All animals were housed under standard conditions, including a 12 hour light-dark cycle with food and water ad libitum. All procedures were performed according to the European Communities Council Directive (86/806/EEC) for the care and use of laboratory animals and were approved by the Regional Ethics Committee CEEA26, Ministére de l'Education Nationale, de l'Enseignement et de la Recherche.

Preparing active agent formulations. The Smo agonist (SAG) and antagonist (SANT) used were those described in Chen et al., "Small molecule modulation of Smoothened activity," *Proc. Natl. Acad. Sci.* 99:14071-14076 (2002), purchased from D&C Chemicals (China). (SAG, product number: DC-8225; SANT-1, product number DC-8327) The active agents were dissolved in dimethyl sulfoxide (10 mM) and subsequently diluted either in culture medium or in 0.9% NaCl to reach the appropriate concentrations. Testosterone was provided by Sigma-Aldrich (France). Testosterone was dissolved in sesame oil (1 mg/ml) and then diluted to obtain the desired steroid hormone concentrations.

Immunostaining experiments. The primary antibodies used for immunostaining were as follows: Oligodendcyte Transcription Factor 2 (Olig2) (Rabbit, Millipore; mouse, Millipore), myelin basic protein (MBP), (Rabbit, Millipore); anti-NG2 (rabbit, Millipore); Adenomatus Polyposis Coli (APC/CC1) (mouse, Calbiochem), BrdU antibody (rat, Abeam); Glial Fibrillary Acidic Protein (GFAP), (Rabbit, Dako; mouse, Sigma); Ionized calcium binding adaptor molecule 1 (Iba1, rabbit, Wako); Arginase-1 (goat, Santa-Cruz), Protolipid Protein (PLP), (mouse, Millipore); Platelet-Derived Growth Factor Receptor alpha (PDGFRa), (mouse, Millipore); Neurofilament 200 (NF200), (chicken, Neuromics); Ki67 (mouse monoclonal; BD Pharmingen). The secondary antibodies used were: goat anti-rabbit cyanine 3 conjugated (Jackson Immunoresearch); goat anti-mouse Alexa 488, anti-rabbit Alexa 633, anti-chicken Alexa 546; donkey anti-goat Alexa 546 (Thermo Fisher Scientific).

Image Acquisition and Analysis. Images were taken using the microscope analyzing system Axiovision 4.2 (Carl Zeiss, Inc.), the confocal Zeiss LSM 510-Meta Confocor 2 and the scanner imager with the CaseViewer software. Analyses were performed with ImageJ software. At least 10 sections per mouse were analyzed and data are the mean of 3-5 mice. For the brains derived from the lysolecithin (LPC)-injected animals, immunofluorescent-positive cells or areas were determined in one every other 5 sections throughout the whole demyelinated lesion per mouse and averaged for each animal. The lesion surface was determined by measuring the area of the nuclear densification (correlated with myelin loss visualized by MBP or PLP staining) one every other 5 slices through the whole demyelinated lesion.

Electron microscopy. Ultrathin sections of lumbar spinal cords were examined using transmission electron microscope (1011 JEOL) equipped with a Gatan digital camera. The g ratio (the ratio between the axon diameter and fiber diameter corresponding to myelin sheath+axon diameter) was estimated by measuring the minimum and maximum axon diameter and fiber diameter for each axon using ImageJ software. At least 300 randomly chosen myelinated axons were evaluated for each animal.

RT-qPCR analysis. At least four animals of each gender and age were sacrificed by decapitation. Dorsal telencephalons were dissected and frozen in liquid nitrogen for further processing. Total RNA was isolated by using the Trizol Technique (Thermo Fisher Scientific) and RNeasy Mini Kit (Qiagen). Reverse Transcription was performed using the High Capacity cDNA Reverse Transcription kit (Applied Biosystems). Quantitative real-time PCR was carried out by using the TaqMan Gene expression Master Mix (Thermo Fisher Scientific) and gene expression was analyzed with the 7300 Systems SDS Software (Applied Biosystems) normalized to reference genes GAPDH. TaqMan probes were as follows: GAPDH, Mm99999915_m1; MBP, Mm01266402_m1; Shh, Mm00436528_m1; Gli1, Mm00494654; AR, Mm00442688.

Statistical analysis. Data are expressed as means±S.E.M. Statistical analysis was performed with GraphPad Prism 6.0. One way ANOVA was used for statistical significance evaluation. The levels of significance were *$p<0.05$, $p<0.01$, *$p<0.001$.

Example 1

Figure 1B:
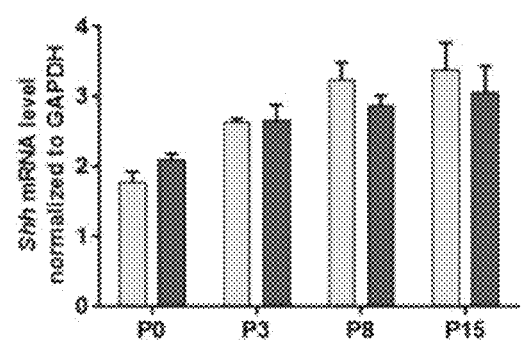
Figure 1C:
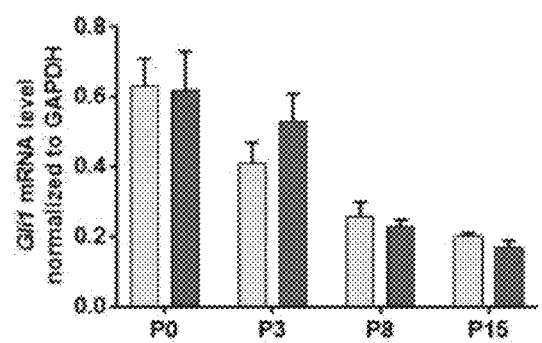
Figure 1D:
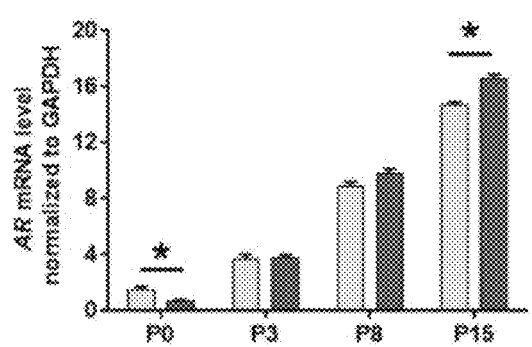

Functional Interaction Between Hedgehog and Androgen Signaling During Early Postnatal Myelination The present inventors identified a functional interaction between Hedgehog (Hh) and androgen signaling during the early period of postnatal myelination of the telencephalon. In this regard, the expression profiles of transcripts encoding myelin basic protein (Mbp), Hh signaling components (Shh, Gli1), and the androgen receptor (AR) were studied, using the dorsal forebrain of male and female mice from birth to postnatal day 15 (P15). This period encompasses the neonatal wave of oligodendrogenesis, the maturation of the generated oligodendrocyte precursor cells (OLPs) and the physiological process of myelination in the dorsal forebrain. Kessaris et al., Nature Neuroscience 9:173-179 (2006). Mbp transcription was detected at a very low level at P3 and then displayed an approximately 10- and 60-fold increase at P8 and P15, respectively, as shown in FIG. 1A. Shh mRNA increased slightly but significantly until P8 before reaching a plateau, as shown in FIG. 1B. Unexpectedly, Gli1 progressively decreased between P0 and P15, as shown in FIG. 1C. In contrast, androgen receptor (AR) transcription was detected at a low level at birth, but sharply increased until P15, reaching a level 10- to 24-fold higher in males and females, respectively, as shown in FIG. 1D. The transcription of Shh, Gli1 and Mbp was not significantly different according to the sex of the animals at the studied time points. In contrast, although the expression of AR was significantly higher in males compared to females at birth, AR was transcribed in a comparable manner regardless of the sex of the animals at P3 and P8, and AR expression was unexpectedly displayed a slightly but significantly higher level in females compared to males at P15, as shown in FIG. 1D. These results indicate that the androgen and Hedgehog signaling pathways might communicate to regulate the myelination process.

SAG+T Promotes Proliferating Oligodendrocytes During Developmental Myelination

SANT+T Promotes Differentiation Of Myelin-Producing Oligodendrocytes During Developmental Myelination Primary glial cell cultures were prepared from the dorsal telencephalon of newborn (P1) male mice as previously described in Feutz et al, J. Neurocytol, "Isolation and characterization of defective jimpy oligodendrocytes in culture", 24:865-877 (2001). Briefly, meninges are removed, and the dorsal telencephalons are microdissected and mechanically dissociated in DMEM supplemented with 10% calf serum, penicillin (50 U/ml), and streptomycin (50 µg/ml) (Thermo Fisher Scientific, France). The cell suspension is plated in a 24-well plates containing 0.5 ml of cultured medium coated with 30 µg/ml poly-1-lysine (Sigma-Aldrich). Cultures containing astrocytes, oligodendrocytes (OLs) and microglia cells are then incubated in 5% CO2 and 95% air in a humidified atmosphere (90%) at 37° C.

At 5 days in vitro (DIV), the culture medium of mixed primary glial cells was replaced by fresh medium supplemented with one of (i) the Smo agonist SAG (0.1 or 1 µM), (ii) SANT-1 (0.1 µM), (iii) testosterone (T, 1 µM), (iv) SAG (0.1 or 1 and testosterone (1 µM), (v) SANT-1 (0.1 µM) and testosterone (1 µM), or (vi) the drug carriers as control. The supplemented culture medium was replaced every other day with a fresh solution. At 12 DIV, the cells were fixed for 20 minutes with 4% paraformaldehyde (PFA) in PBS, then permeabilized with 0.025% Triton X-100 for 10 minutes and blocked for 1 hour with Sea Block buffer (Thermo Fisher Scientific).

The cells were immunostained for BrdU and Olig2. For immunostaining, after overnight incubation with the primary antibodies at 4° C. followed by 3 washes in PBS, the cells were incubated with the appropriate secondary antibodies for 2 hours before washing with PBS and the addition of Fluoromount (Vector, cliniciences, France) as the mounting medium. Images were acquired with immunofluorescence microscopy as described above. (Data not shown). Quantification of Olig2+BrdU+ was evaluated by analyzing 3-4 independent cultures for each test condition, and these results are reported in FIGS. 2A-2B.

Figure 2A:
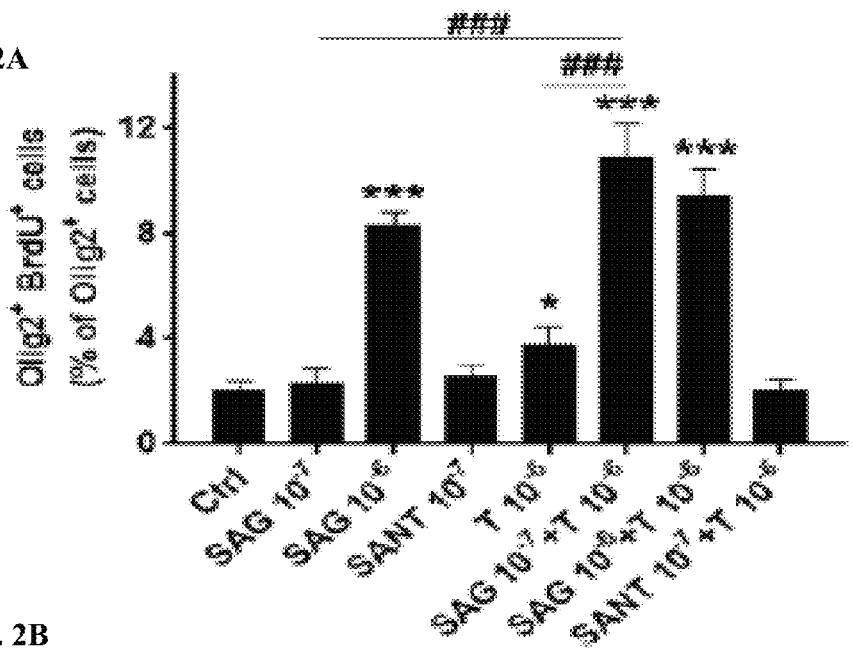
FIGS. 2A-2B show the functional interaction between the Hedgehog and testosterone signaling pathways in vitro for the control of OPC proliferation and differentiation.

FIG. 2A shows the quantification of Olig2$^+$ cells which have incorporated the proliferation marker BrdU 2 hours before the end of the culture, and indicates a synergic effect with SAG (0.1 µM) and testosterone (1 µM). FIG. 2A also show that in the absence of the active agents, Olig2$^+$ BrdU$^+$ proliferating glial cells represent 2.0±0.4% of the total number of Olig2$^+$ cells, while the percentage of proliferating cells was significantly increased compared to control with SAG (1 µM) or testosterone (1 µM), reaching 8.4±0.5 (p=6.93E-09) and 3.8±0.6% (p=0.04) of total Olig2 cells, respectively.

Figure 2B:
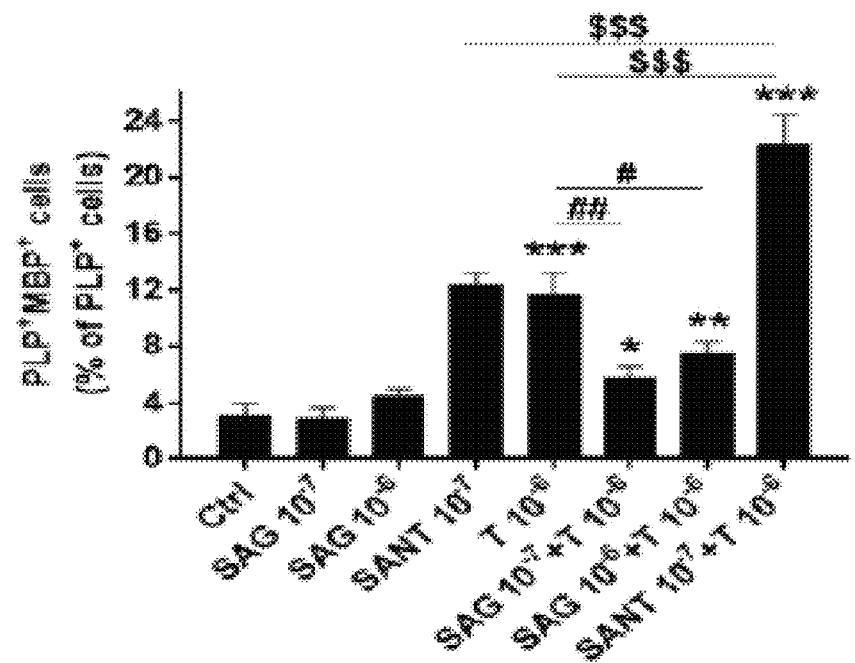

To analyse differentiation of myelin producing cells, the primary mixed glial cells were derived from Plp-EGP mice and cultured as described above. Detection of PLP+ cells co-expressing MBP was performed by using primary mixed glial cells derived from Plp-EGP mice and immunostaining for Mbp. Immunofluorescence images were acquired as described above and the number of PLP$^+$ cells co-expressing MBP were evaluated. FIG. 2B shows that SANT and testosterone administered together to primary mixed glial cells induce significantly higher levels of MBP expression than that induced by each active agent used alone (p=0.001). The immunostaining data (not shown) reveal that testosterone (1 µM) and SANT (0.1 µM) highly increase the number of plp$^+$GFP$^+$ cells that co-express Mbp. The Smo agonist SAG (0.1 µM or 1 µM) did not modify Mbp expression when it was used alone. However, both concentrations of SAG induced a slight but significant decrease of testosterone-mediated OL differentiation. Remarkably, testosterone and SANT-mediated differentiating effects appear to be additive when the drugs are used together. The inhibition of Smo by SANT (0.1 µM) or testosterone (T, 1 µM) led to a 4-fold increase in the percentage of PLP$^+$ cells co-expressing MBP as compared to the control condition (12.4±0.8 for SANT1, p=6.09E-07 and 11.7±1.5 for testosterone, p=0.0005).

FIG. 2B further shows that when SANT and testosterone are used together, a 7-fold increase is observed in the percentage of mature OLs as compared to the control (22.3±2.1 vs 3.0±0.9; p=2.22E-06). On the other hand, the Smo agonist SAG (0.1 µM or 1 µM) did not modify Mbp expression when it was used alone. However, both concentrations of SAG induced a slight but significant decrease of testosterone-mediated OL differentiation. Remarkably, testosterone and SANT-mediated differentiating effects appear to be additive when the drugs are used together. While not being bound by theory, these results suggest that the hedgehog signaling blockade potentiates testosterone-induced maturation of oligodendrocyte progenitor cells (OPCs) into MBP+ myelinating OLs.

To further investigate whether SANT+T promotes differentiation of myelin-producing oligodendrocytes during developmental myelination, P3 male pups were subcutaneously treated with the SANT and/or testosterone every other day (n=3-5 animals per group) from the third to the tenth postnatal day. SANT was used at a concentration of 20 µg/g pup weight, while testosterone was used at 20 µg for each administration. The drugs were injected subcutaneously every other day from postnatal day 3. At P10, the pups were deeply anesthetized and perfused with PFA 4%. The brain was removed, post-fixed for 1 hour in PFA 4% and cryo-preserved in sucrose 30% before freezing and cryostat sectioning (14 µm). Subsequently, immunostaining for Olig2, Olig2/APC, Olig2/PDGFRα, and MBP/NF200 of the brain slices was performed at the level of the subventricular zone and the adjacent corpus callosum (cc) of postnatal day 10 male pups treated with the Smo agonist SAG, the Smo antagonist SANT, and the steroid hormone testosterone (T). Images were acquired with immunofluorescence microscopy as described above (data not shown), and the different cell populations were quantified as shown in FIG. 3A-3D.

Figure 3A:
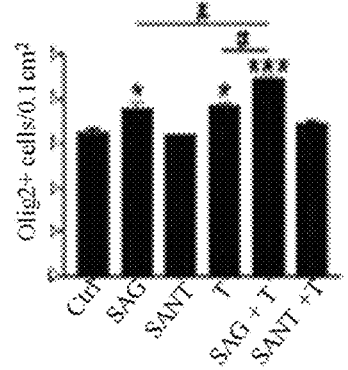
FIGS. 3A-3D show that blocking Hedgehog signaling potentiates the differentiation of OPCs induced by testosterone in vivo during the last wave of oligodendrogenesis in the dorsal forebrain. Postnatal day 10 male pups were treated with the Smo agonist SAG, the Smo antagonist SANT-1, the steroid hormone testosterone (T), SAG and T, SANT-1 and T, or treated with carrier as control (Ctrl).
Figure 3B:
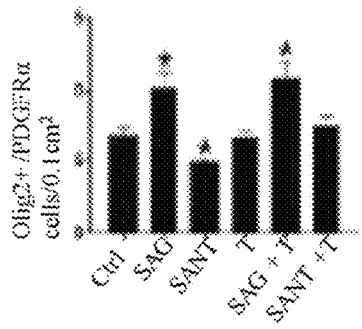
Figure 3C:
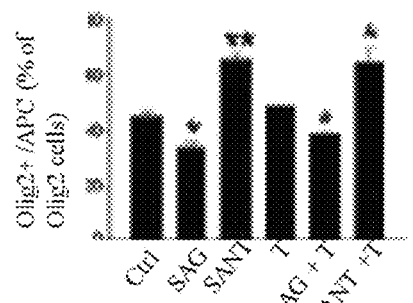
Figure 3D:
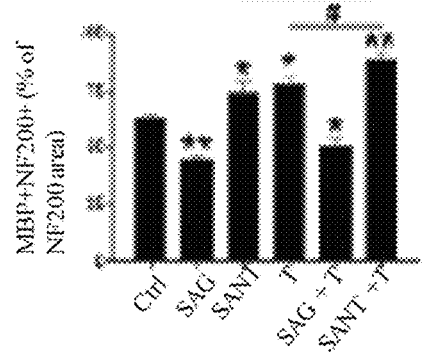

FIG. 3D shows that combined treatment of testosterone and SANT-1 promoted the production of myelin sheaths in male pups at P10. In the absence of the active agents, the area occupied by MBP (the myelinated area) corresponded to 62.4±2.2% of the total area occupied by the axons expressing the neurofilament protein NF200. See FIG. 3D. In the presence of SANT or testosterone, the percentage of myelinated area reached a significantly higher value of 75.1±4.3 (SANT) (p=0.04) and 78.0±4.1% (T) (p=0.01). See FIG. 3D. When SANT and testosterone were concomitantly injected into the pups, the area occupied by the myelinated $NF200^+$ MBP axons reached 88.9±2.7%, a value significantly greater than obtained with SANT or testosterone alone (p=0.03 vs SANT, p=0.05 vs testosterone).

Thus, these data indicate that the Hedgehog and the androgen signaling pathways functionally interact during the neonatal wave of oligodendrocyte precursor cell production, and during the subsequent differentiation of these cells into myelinating oligodendrocytes.

Overall, the results indicate that the combination SAG and testosterone promotes proliferation of oligodendrocyte precursor cells but SAG inhibits testosterone-induced maturation of these cells into myelin-producing oligodendrocytes.

Example 2

Smo Activation by SAG Promotes Production of New Mature Oligodendrocytes and Precocious Increase of Pro-Regenerative Microglia in the LPC Model of Demyelination.

The effect of Smo activation by the Smo agonist SAG on demyelination was investigated as follows. LPC-induced demyelination was performed as previously described in Ferent et al., J. Neuroscience 33:1759-1772 (2013), in the absence or presence of SAG, in young male adult mice. Briefly, demyelinating lesions were induced unilaterally by stereotaxic injections of 2 μl of a solution containing LPC 1% (Sigma-Aldrich) along with SAG (0.2 μM) or the corresponding vehicle, into the right corpus callosum by using a Hamilton syringe specifically dedicated for neural surgery (NH BIO, France). The injection was performed at the following coordinates (to the bregma): anteroposterior (AP)+1 mm, lateral+1 mm, dorsoventral (DV) −2.2 mm. The brain was removed from deeply anesthetized mice and transcardially perfused with 4% PFA. The tissue was post-fixed for 4 hours in a fresh 4% PFA solution before being cryopreserved in 30% sucrose, frozen in liquid nitrogen and cryostat sectioned (14 μm). 4-5 mice were used per time point for each treatment condition. Mice were sacrificed at 2 and 10 days post-lesion (dpl), and prepared for immunostaining of PDGFRα, Olig2/APC, Ki67/PDGFRα, GFAP, and Iba1/Arg1. Images of immunostaining were acquired using immunofluorescence microscopy (data not shown), and the results were quantified by evaluating number of cells per surface unit for PDGFRα (FIG. 4A), Olig2/APC (FIG. 4B), Ki67/PDGFRα (FIG. 4C), GFAP (FIG. 4D), Iba1/Arg1 (FIG. 4E)

Remarkably, it was found that at 10 dpl SAG-treated animals displayed a 2-fold increase in PDGFRα+ cells compared to the controls (121±11 vs 65±5, p=0.008; FIG. 4A). Furthermore, the densities of Olig2+APC+ mature OLs were found to be significantly higher in the presence of SAG than in the control condition (83±7 vs 59±1, p=0.027, FIG. 4B). Since the proportion of mature OLs appeared not significantly different between the SAG-treated and control animals, it appears that SAG does not likely promote OPC differentiation.

At the earlier time point (2 dpl), new OPCs start to be recruited and highly proliferate in the lesion while the tissue already displays a high inflammatory level. It was found that SAG treatment caused an increase in the densities of proliferating Ki67+ PDGFRα+ OPCs compared to the control condition (39±2 vs 28±2, p=0.007, FIG. 4C, left panel). Interestingly, the total number of PDGFRα+ OPCs remained unchanged indicating that SAG induced OPCs to enter the cell cycle. FIG. 4C, right panel.

To investigate a possible effect on the inflammatory cells, astrocytes and microglia were analyzed at the same time point. The area occupied by GFAP+ astrocytes tended to be decreased in the presence of SAG although not in a significant manner. See FIG. 4D. Iba1+ microglia was found to be unaffected by the presence of SAG as well. However, it was found that the density of the sub-population of microglia called "pro-regenerative" and characterized by the expression of Arginase-1 (Arg1) was enhanced by 2-fold in the SAG-treated mice (103±7 vs 54±8, p=0.035, FIG. 4E, left panel). Furthermore, the proportion of Iba1 microglia co-expressing Arg1 was increased two-fold by SAG treatment (58±5 vs 25±2, p=0.017; FIG. 4E, right panel). These results indicate that Hedgehog signaling activation by Smo agonists promotes the pro-regenerative potential of activated microglia.

Figure 6:
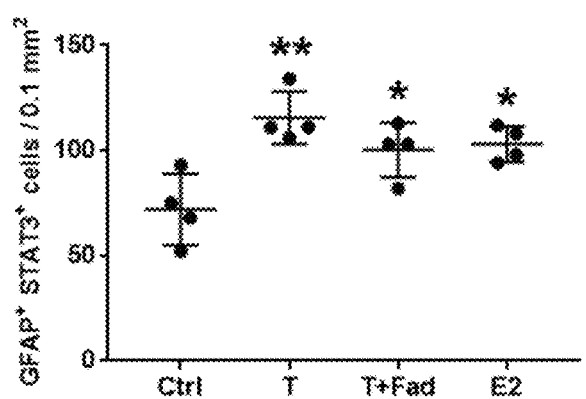
FIG. 6 shows that testosterone (T) and estradiol (E2), its aromatase-mediated conversion product whose generation is prevented by the presence of the aromatase inhibitor fadrozole (Fad), both regulate the expression of phosphorylated STAT3 in astrocytes. The values reported are the means±SEM from n=4 animals. *, p<0.05; **, p<0.01.

Since testosterone promotes astrocyte recruitment during remyelination, we investigated whether testosterone controls the phosphorylation of signaling transducer and activator of transcription 3 (STAT3), which is a mediator of signaling pathways important for myelin regeneration in astrocytes. The quantification of phosphorylated STAT3-expressing astrocytes was performed in brain slices derived from castrated male mice demyelinated by stereotaxic injection of lysolecithin after 7 days of treatment with (1) intranasal administration of testosterone (T) at 0.2 mg/day, (2) intranasal testosterone together with fadrozole (Fad) administered per oral route at 260 μg/kg, or (3) intranasal estradiol (E2) at 0.05 mg/day (n=4 per group). At 7 days post-lesion in the LPC-induced demyelination model, testosterone increased the number of $GFAP^+$ astrocytes expressing phosphorylated STAT3. The latter is important for both remyelination and astrocyte reactivity, which is similar to activated microglia involved in local inflammation. This effect appeared to involve testosterone aromatization to estradiol because the effect of testosterone could be inhibited by fadrozole, an inhibitor of the aromatase enzyme, as shown in FIG. 6. Moreover, estradiol also could increase the number of phosphorylated STAT3-expressing astrocytes to a similar extent as testosterone, as shown in FIG. 6.

Therefore, SAG and testosterone appeared to promote the pro-regenerative phenotypes of distinct inflammatory cells, microglia and astrocytes, respectively. Such complementary activities may likely be additive for decreasing local inflammation.

Example 3

SAG+T Mitigates Experimental Autoimmune Encephalomyelitis.

Castrated male mice at age of 9-10 weeks were maintained for one week for acclimatization prior to experimental autoimmune encephalomyelitis (EAE) (n=10 animals per condition). The pathology was induced according to the instructions from the provider (Hooke Laboratories, MA, USA). Briefly, mice were immunized by subcutaneous injection of an emulsion of $MOG_{35-55}$ peptide (myelin oligodendrocyte glycoprotein/MBP fragment 35-55) in complete Freund's adjuvant (at two sites using 0.1 ml of the preconditioned mixture for each site) followed on the same day (Day 0) by a first intraperitoneal injection of pertussis toxin in PBS and by a second one on Day 1 (250 ng/dose). The mice were scored blindly once a day starting at Day 7 post-immunization until Day 30 according to the following scale: 0.0=no obvious changes in motor function; 0.5=tip of tail is limp; 1.0=limp tail; 1.5=limp tail and hind leg inhibition; 2.0=limp tail and weakness of hind legs or signs of head tilting; 2.5=limp tail and dragging of hind legs or signs of head tilting; 3.0=limp tail and complete paralysis of hind legs or limb tail with paralysis of one front and one hind leg; 3.5=limp tail and complete paralysis of hind legs and animal unable to right itself when placed on its side; 4.0=limb tail, complete hind leg and partial front leg paralysis with minimal moving and feeding; 4.5=complete hind and partial front leg paralysis with no movement around the cage with the animal appearing no more alert; 5.0=extreme paralysis which requires euthanasia of the animal.

The mice that developed EAE were randomly assigned into vehicle, SAG, testosterone or SAG+testosterone treatment groups in order to constitute groups with similar time of EAE onset and similar onset scores (n=10 animals per group). The active agents were administered at the onset of clinical symptoms until Day 30 after immunization. Testosterone was administered via the intranasal route (0.2 mg/day in a volume of 2.5 µl in each nostril) in an oleogel composition as described above. SAG was administered orally by gavage (15 µs/g of mouse weight) every other day.

The animals were sacrificed by ketamine overdose. The spinal cord/vertebrae was removed and lumbar spinal cord/vertebrae samples were treated according to the requirements of the various histological procedures. For immunostaining, the spinal cord/vertebrae fragments were post-fixed in PFA 4% for 24 hrs. The spinal cords were removed from the vertebral column, processed in an ethanol/xylene bath and embedded in paraffin blocks. 7-µm sections were then obtained using a microtome (Leica) and allowed to dry on glass slides overnight at 37° C. For electron microscopy, the spinal cord/vertebrae fragments were post-fixed in a mixture of PFA 2% and glutaraldehyde 2% for 5 days. The spinal cords were removed from the vertebral column, post-fixed in cacodylate-buffered 1% osmium tetroxide for 1 hour at 4° C. and in 2% uranyl acetate for 1 hour at room temperature, and then dehydrated by serial dilutions of ethanol and embedded in epoxy resin. Ultrathin sections were contrasted with a saturated uranyl acetate solution.

Figure 5A:
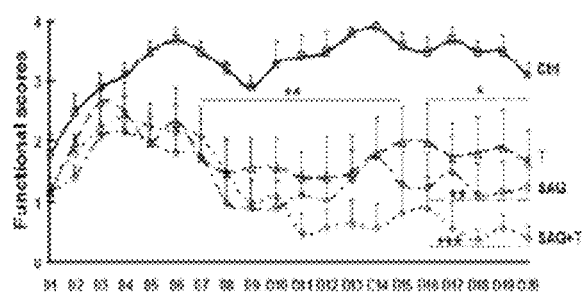
FIGS. 5A-5F show that combination therapy based on the simultaneous pharmacological activation of Smo-mediated Hh signaling and androgen signaling highly mitigates the course of experimental autoimmune encephalomyelitis (EAE).

FIG. 5A shows the improved clinical scores observed after treatment with both SAG and testosterone, as compared to treatment with each active agent separately. At days 18-19, animals in the three groups reached the score 1.0 maintained until day 21 for each treatment. Between days 21 and 30, testosterone-treated animals showed a relapse and the clinical score reached a value close to 2.0. In contrast, SAG-treated animals were stabilized around the significantly lower score of 1.0. Remarkably, the drug combination fluctuated between the lowest clinical scores 0.5 and 1.0, suggesting improved clinical scores by the combination of SAG and testosterone compared to using these drugs alone. See FIG. 5A.

Figure 5C:
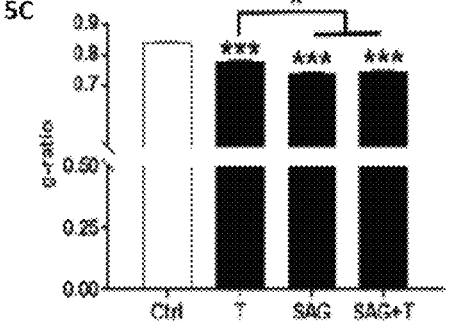
Figure 5B:
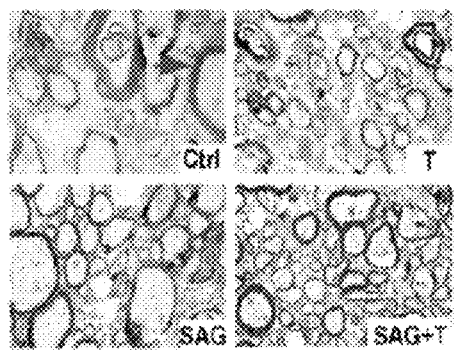
Figure 5D:
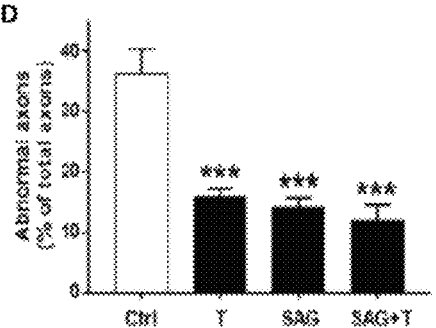

To investigate the mechanisms involved in mitigating EAE, we examined the myelin levels and axon pathology at 30 days post EAE induction in each condition. Electron microscopy images showed that the spinal cords from the animals treated with SAG and testosterone alone or in association had much higher density of myelinated axons, and abnormal structures were only occasionally observed. See FIG. 5B. Next, shows the g-ratio (axon diameter/total outer diameter of the myelinated fiber) of at least 300 small calibre axons (≤2.5 µm) per animal (n=3 for each condition) was determined and shown in FIG. 5C. In the spinal cords derived from the control EAE animals, the g-ratio value (0.834±0.004) was significantly higher than the values determined for the animals treated by testosterone (0.773±0.003, $p<10^{-10}$), SAG (0.737±0.005, $p<10^{-10}$) or the drug combination (0.743±0.005, $p<10^{-10}$). Interestingly, FIG. 5C further shows that the administration of SAG alone or in association with testosterone led to a significantly lower g-ratio than testosterone alone ($p<10^{-5}$); whereas, the effect of SAG alone was not significantly different from the effect induced by the drug combination. Then, the numbers of abnormal structures (as described above) were evaluated. See FIG. 5D. Higher percentages of abnormal axons were detected in the spinal cord of the control EAE animals (36.4±4.0) than in the testosterone (15.8±1.4, p=0.0004), SAG (14.0±1.7, p=0.0002) or SAG+testosterone (11.8±2.6, p=0.0001) treated mice.

In conclusion, SAG and testosterone administered separately or substantially simultaneously promote functional recovery associated with regeneration of myelin and neuroprotection.

Figure 5E:
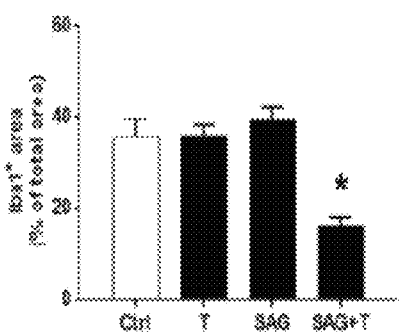
Figure 5G:
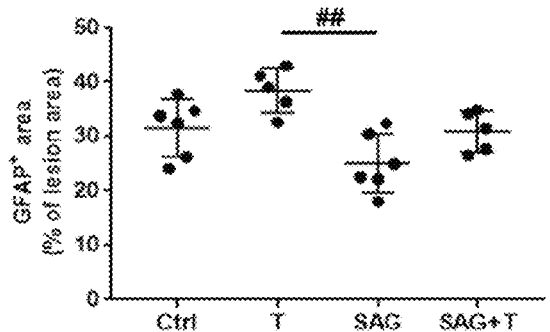
FIG. 5G shows the quantification of the GFAP-positive area as the percentage of the lesion area in the spinal cord of the EAE animals treated with testosterone and SAG, separately or simultaneously.
Figure 5F:
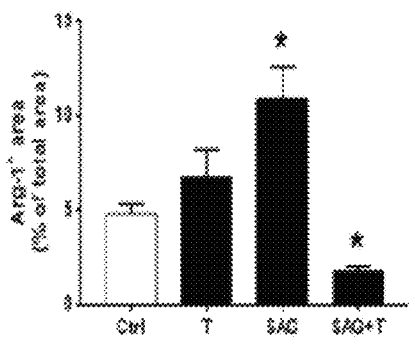

Since the various effects observed for the combination treatment tended to be higher than the effects of SAG alone, the consequences of the active agents on the microglial cells was investigated. Spinal cord slices from EAE animals were immunostained with Iba1 and Arg1 antibodies, which allowed the visualization of the whole activated microglia and its pro-regenerative phenotype, respectively. Images were acquired using immunofluorescence microscopy (data not shown), and the activated microglia area was quantified and visualized as histograms in FIG. 5E-F. It was found that the control EAE mice had a high amount of activated $Iba1^+$ microglia present in the spinal cord, but these cells were not polarized towards their pro-regenerative phenotype. Neither testosterone nor SAG was found to significantly modify the total density of activated microglia in the spinal cord as shown in FIG. 5E. However, SAG (10.9±1.7, p=0.03) but not testosterone (6.8±1.4) promoted microglia polarization towards the Arg1+ anti-inflammatory and pro-regenerative phenotype as compared to control (4.8±0.5) as shown in FIG. 5F. Unexpectedly, activated microglia collapsed as a whole compared to the control when the active agents were used simultaneously (1.8±0.2, p=0.03, FIG. 5F), indicating that the combination appears to solve a pathological microglia activation.

In order to assess the effects of testosterone and SAG alone or in combination in astrocytes, spinal cord from EAE animals were also immunostained with GFAP antibody. Quantifications performed in immunofluorescent microscopy images indicated that testosterone and SAG tend to increase or decrease GFAP-positive area, respectively. The GFAP-positive area in EAE animals treated with testosterone, SAG, or the combination of testosterone and SAG was not significantly different from the GFPA-positive area in the control group. However, testosterone (38.8±1.8) induced a significantly higher GFAP staining than SAG (25.1±2.2, p=0.001). The co-administration of testosterone and SAG led to a GFAP-positive area comparable to the GFAP-positive area in the control group as shown in FIG. 5G, suggesting that testosterone and SAG may regulate different subsets of GFAP-positive astrocytes potentially involved in the beneficial effects of the combination therapy.

Figure 5H:
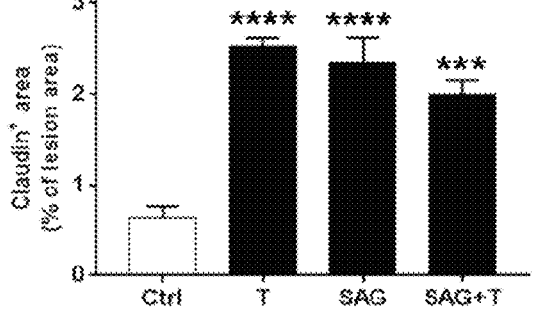
FIG. 5H shows the quantification of the Claudin-positive area as the percentage of the lesion area in the EAE animals treated with testosterone and SAG, separately or simultaneously. Data reported are the mean±SEM (n=10 mice per condition). *, p≤0.05, , p≤0.01, *, p≤0.001, ##, p=0.001, ****, p<0.0001, one-way ANOVA with Tukey's multiple comparison test.

Since lymphocyte recruitment into the brain across vascular endothelial cells of the blood brain barrier represents an important event in the pathogenesis of the EAE model and multiple sclerosis itself, the effects of testosterone and SAG used alone or in combination on the permeability of the blood brain barrier were assessed. To assess the permeability of the blood brain barrier, an antibody directed to the tight junction protein Claudin 5 was used, since the proteins of this family confer to endothelial cells an ability to strictly regulate the passage of soluble and cellular elements between the blood and the central nervous system. Quantifications performed in immunofluorescent microscopy images indicated that testosterone (2.53±0.09, $p<0.0001$), SAG (2.35±0.27, $p<0.0001$) and the combination therapy (2.03±0.15, $p<0.0003$) induced a highly significant increase in the expression of Claudin 5 compared to the control condition (0.65±0.11) with no significant difference between the treatments, as shown in FIG. 5H. Thus, testosterone and SAG used alone or in combination appear to exhibit a beneficial activity towards restoring the efficiency of the blood brain barrier.

Overall, the results indicate that combination treatment with an Smo agonist and a steroid hormone has synergistic therapeutic effects in one of the most relevant models for MS.

What is claimed is:

1. A method of promoting remyelination in a subject in need thereof, comprising administering to the subject an effective amount of a steroid hormone and a Smoothened agonist (Smo agonist).

2. The method according to claim 1, wherein the steroid hormone is selected from an androgen receptor ligand, a progesterone receptor ligand, an estrogen receptor ligand, dehydroepiandrosterone, a selective hormone receptor modulator, a selective androgen receptor modulator, a selective estrogen receptor modulator, and a selective progesterone receptor modulator.

3. The method according to claim 1, wherein the steroid hormone is selected from testosterone, progesterone, allopregnanolone, and estradiol.

4. The method according to claim 1, wherein the steroid hormone is testosterone.

5. The method according to claim 1, wherein the steroid hormone is testosterone and the Smo agonist is 3-Chloro-N-[trans-4-(methylamino)cyclohexyl]-N-[[3-(4-pyridinyl)phenyl]methyl]benzo[b]thiophene-2-carboxamide (SAG).

6. The method according to claim 1, wherein the steroid hormone and the Smo agonist are administered in separate compositions, substantially simultaneously or sequentially.

7. The method according to claim 1, wherein the steroid hormone and the Smo agonist are administered in the same composition.

8. The method according to claim 1, wherein one or both of the steroid hormone and the Smo agonist is administered intranasally in an intranasal pharmaceutical composition that further comprises: (a) at least one lipophilic or partly lipophilic carrier present in an amount of from about 60% to about 98% by weight of the formulation; (b) at least one compound having surface tension decreasing activity present in an amount of from about 1% to about 20% by weight of the formulation; and (c) at least one viscosity regulating agent present in an amount of from about 0.5% to about 10% by weight of the formulation.

9. The method according to claim 8, wherein the steroid hormone is testosterone and the Smo is agonist 3-Chloro-N-[trans-4-(methylamino)cyclohexyl]-N-[[3-(4-pyridinyl)phenyl]methyl]benzo[b]thiophene-2-carboxamide (SAG).

10. The method according to claim 1, wherein one or both of the steroid hormone and the Smo agonist is administered intranasally in an intranasal pharmaceutical composition comprising a porous excipient, wherein the steroid hormone and/or the Smo agonist is/are loaded onto a surface of the porous excipient located inside pores of the porous excipient.

11. The method according to claim 10, wherein both the steroid hormone and the Smo agonist are loaded onto a surface of the porous excipient located inside pores of the porous excipient.

12. The method according to claim 11, wherein the steroid hormone is testosterone and the Smo agonist is 3-Chloro-N-[trans-4-(methylamino)cyclohexyl]-N-[[3-(4-pyridinyl)phenyl]methyl]benzo[b]thiophene-2-carboxamide (SAG).

13. The method according to claim 1, wherein the subject is a human, a non-human primate, a dog, a cat, a cow, a sheep, a horse, a rabbit, a mouse, or a rat.

14. A method of treating a disease of the central nervous system, comprising administering to the subject an effective amount of a Smoothened agonist (Smo agonist).

15. The method according to claim 14, wherein the disease of the central nervous system is inflammation, and the Smo agonist reduces inflammation in brain tissue.

16. The method according to claim 14, wherein the disease of the central nervous system is selected from multiple sclerosis, amyotrophic lateral sclerosis, Devic's disease, inflammatory demyelinating diseases, central nervous system neuropathy, central pontine myelinolysis, myelopathies, tabes dorsalis, syphilitic myelopathy, leukoencephalopathies like progressive multifocal leukoencephalopathy, Leukodystrophies, and Alzheimer's disease; or a demyelinating disease of the peripheral nervous system selected from Guillain-Barré syndrome, chronic inflammatory demyelinating polyneuropathy, Anti-MAG peripheral neuropathy, Charcot-Marie Tooth disease, hereditary neuropathy with liability to pressure palsy, peripheral neuropathy, myelopathy, optic neuropathy, and progressive inflammatory neuropathy.

17. An intranasal pharmaceutical composition, comprising a steroid hormone and an Smo agonist.

18. The composition according to claim 17, wherein the composition further comprises (a) at least one lipophilic or partly lipophilic carrier present in an amount of from about 60% to about 98% by weight of the formulation; (b) at least one compound having surface tension decreasing activity present in an amount of from about 1% to about 20% by weight of the formulation; and (c) at least one viscosity regulating agent present in an amount of from about 0.5% to about 10% by weight of the formulation.

19. The composition according to claim 17, wherein the composition comprises a porous excipient, wherein one or both of the steroid hormone and the Smo agonist is/are loaded onto a surface of the porous excipient located inside pores of the porous excipient.

20. The composition according to claim 17, wherein the steroid hormone is testosterone and the Smo agonist is 3-Chloro-N-[trans-4-(methylamino)cyclohexyl]-N-[[3-(4-pyridinyl)phenyl]methyl]benzo[b]thiophene-2-carboxamide (SAG).

* * * * *